United States Patent [19]
Corliss et al.

[11] 3,942,539
[45] Mar. 9, 1976

[54] ANTISEPTIC CLEANSING DENTAL FLOSS
[76] Inventors: Joseph J. Corliss, c/o George Spector, 3615 Woolworth Bldg., 233 Broadway; George Spector, 3615 Woolworth Bldg., 233 Broadway, both of New York, N.Y. 10007

[22] Filed: Apr. 8, 1974
[21] Appl. No.: 458,908

[52] U.S. Cl. .................................. 132/79 E; 132/91
[51] Int. Cl.² .......................................... A45D 40/00
[58] Field of Search ............ 132/79 E, 89, 91, 92 A

[56] References Cited
UNITED STATES PATENTS

| 2,667,443 | 1/1954 | Ashton | 132/91 |
|---|---|---|---|
| 3,472,247 | 10/1969 | Borsum et al. | 132/91 |
| 3,699,979 | 10/1972 | Muhler | 132/89 |
| 3,744,499 | 7/1973 | Wells | 132/92 A |
| 3,789,858 | 2/1974 | Pesce | 132/89 |

*Primary Examiner*—G. E. McNeill

[57] ABSTRACT

An improved dental floss which comprises a length at one end that is of conventional dental floss construction and which comprises the remaining length being porous so that when pre-soaked, prior to use, in an antiseptic mouthwash solution, the antiseptic is delivered into remote crevices between the teeth as the floss is used, thus disinfecting these areas for an improved oral hygiene.

4 Claims, 10 Drawing Figures

U.S. Patent  March 9, 1976  3,942,539
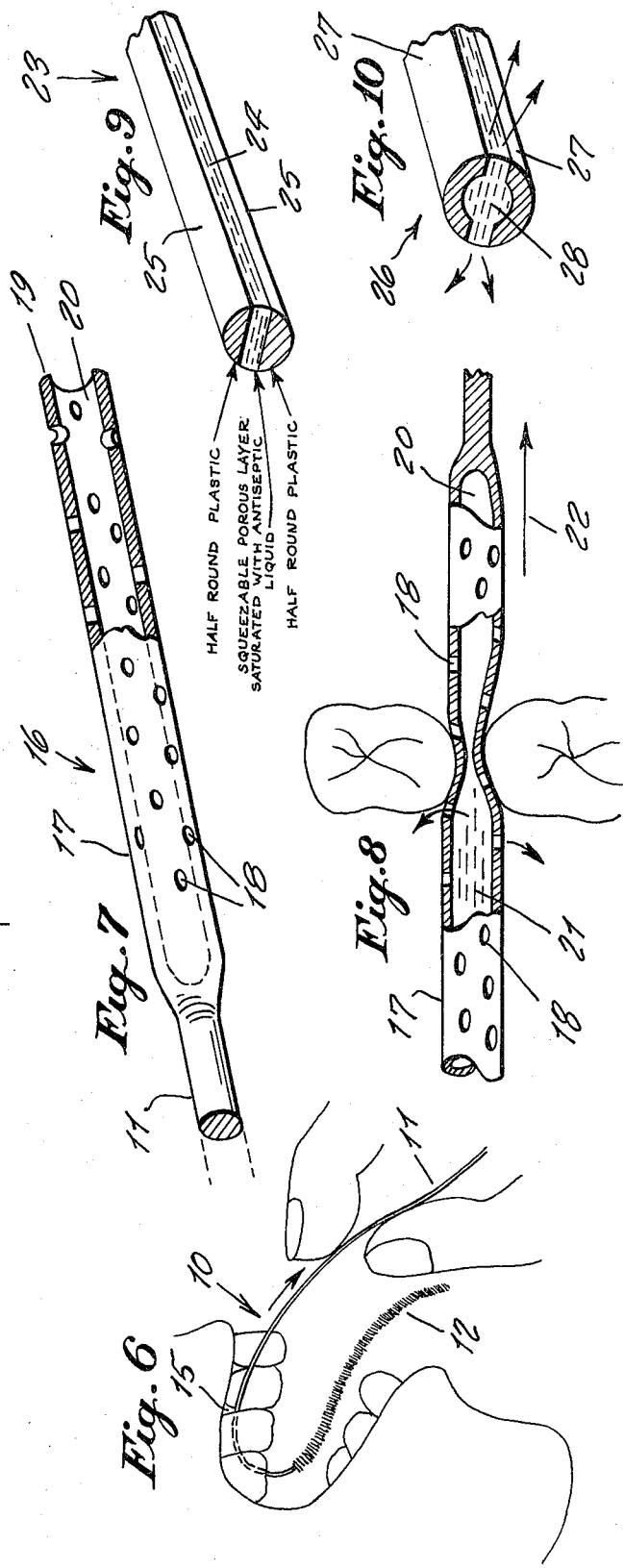

ANTISEPTIC CLEANSING DENTAL FLOSS

This invention relates generally to dental flosses.

A principle object of the present invention is to provide a dental floss of improved type that disinfects remote crevices between the teeth so to preserve a healthy condition of gums and teeth.

Another object is to provide an improved dental floss which delivers antiseptic solution into these hidden remote areas.

Another object accordingly is to provide a dental floss which does the normal function of physically removing food particles from between the teeth and additionally disinfects these areas.

Other objects are to provide a dental floss which is simple in design, inexpensive to manufacture, rugged in construction, easy to use and efficient in operation.

These and other objects will be readily evident upon a study of the following specifications and the accompanying drawing wherein:

FIG. 1 is a side view of the invention.

FIG. 2 is an enlarged detail of the regular floss portion thereof.

FIG. 3 is a cross section on line 3—3 of FIG. 2.

FIG. 4 is an enlarged detail of the porous fuss floss portion thereof.

FIG. 5 is a cross section on line 5—5 of FIG. 4.

FIG. 6 shows the invention in use.

FIG. 7 is a detail of a modified design of the invention in which the porous portion is tubular with perforations on its sides so that in use, as shown in FIG. 8, the antiseptic is squeezed out as the floss is pulled between the teeth.

FIG. 9 shows another construction thereof wherein the floss porous portion is sandwich constructed so to allow a thinner structure while retaining the merit of the structure of FIGS. 7 and 8.

FIG. 10 is a further modified design of the structure shown in FIG. 9, so the central layer can hold a larger quantity of anticeptic.

Referring now to the drawing in detail, and more particularly to FIGS. 1 to 6 thereof at this time, the reference numeral 10 represents an antiseptic cleansing dental floss according to the present invention wherein the same includes a length position 11 thereof that is of conventional dental floss design by being very thin so it can be easily introduced into narrow crevices, the surface of portion 11 being smooth such as in conventional flosses.

In the present invention the floss 10 includes a length portion 12 at its other end that is porous in nature. This is accomplished by having portion 12 made either with microscopic transverse openings therethrough, or the surface thereof being roughened, as shown in enlarged FIGS. 4 and 5, so that depressions 13 are formed between jogged microscopic projections 14.

The floss can be made of conventional floss material consisting of a flexible plastic or the like.

In operative use, the floss 10 is first dipped into an antiseptic mouthwash solution so that the solution lodges into depressions 13. In use, the portion 11, being thinner than portion 12, is first inserted into the crevices 15 between the mouth teeth and is then pulled so that the roughened, antiseptic laden portion 12 gets into the crevice where the antiseptic is wiped off on the crevice surfaces thus disinfecting the same so to inhibit germ growth therein.

Thus a floss is provided which disinfects remote areas in addition to physically removing food particles therefrom.

In FIG. 7, a modified design dental floss 16 is shown in which the porous portion 17 is tubular and has side perforations 18 through the tubular wall 19 that communicates with the central opening 20 in which antiseptic solution 21 is lodged during soaking operation, so that in use, as the floss is pulled between the teeth (as shown by arrow 22 in FIG. 8), the solution is squeezed out through the perforations 18 and disinfects the vicinity.

In FIG. 9 another design of floss 23 is of sandwich construction by including a central porous layer 24 between smooth surfaced outside layers 25. The advantage of this construction is that it is easier to manufacture in a very thin size, and only a smooth surface rubs against the gums so that no irritation results. The porous layer is squeezable so the solution readily is dispensed therefrom. Being open on its sides, the solution is quickly soaked up by the layer 24, prior to use. Layers 25 are of flexible plastic.

In FIG. 10 the floss 26 is the same as floss 23 except that the outer layers 27 are even thickness arcuate in cross section so the central layer 28 is thicker at its center in order to hold a larger quantity of solution.

Thus a modified design of the invention are provided.

While various changes may be made in the detail construction it is understood that such changes will be within the spirit and scope of the present invention as is defined by the appended claims.

What is claimed is:

1. An antiseptic dental floss comprising a flexible length of floss having a first portion of thin, smooth, homogeneous conventional floss and a second portion of non-homogeneous compressible material of generally larger diameter than the first portion, wherein said material includes dental floss conbined with fluid antiseptic wherein the floss has means for retaining the antiseptic discharging said antiseptic responsive to external pressure created by drawing the second portion through ones teeth, wherein the said means comprises roughened flexible enterior floss surfaces protruding radially beyond the diameter of the first said portion creating recesses for the deposition, retention and subsequent oozing discharge of antiseptic from the second portion to the teeth surfaces responsive to compressive pressures.

2. A dental floss as in claim 1 wherein the said means comprises a central bore in said second portion filled with antiseptic and including spaced discharge orifices for discharging the antiseptic from the bore to the floss exterior.

3. A dental floss as in claim 2 wherein said means comprises a longitudinal slot extending for a full diameter from one side of the second portion to the opposite diametral side, said slot being filled with a porous flexible material impregnated with antiseptic, whereby compressive pressure on the floss exterior squeezee the antiseptic out from the porous material.

4. A dental floss as in claim 3 wherein the slot includes an axial circular portion.

* * * * *